United States Patent [19]
Bell

[11] Patent Number: 5,703,688
[45] Date of Patent: *Dec. 30, 1997

[54] METHOD AND APPARATUS FOR INSPECTING AND GRADING GARMENTS

[75] Inventor: Cecil Roland Bell, Pinnacle, N.C.

[73] Assignee: Monarch Knitting Machinery Corporation, Glendale, N.Y.

[*] Notice: The term of this patent shall not extend beyond the expiration date of Pat. No. 5,497,235.

[21] Appl. No.: 610,408

[22] Filed: Mar. 4, 1996

Related U.S. Application Data

[63] Continuation-in-part of Ser. No. 371,810, Jan. 12, 1995, Pat. No. 5,497,235.

[51] Int. Cl.$^6$ .............................. G01N 21/84; G01N 21/04
[52] U.S. Cl. .................... 356/430; 356/238; 356/239; 356/394; 250/559.37; 250/559.47; 250/559.12; 250/559.15
[58] Field of Search .................... 356/420, 238, 356/239, 394; 250/559.42, 559.12–559.15, 559.39

[56] References Cited

U.S. PATENT DOCUMENTS

| | | | |
|---|---|---|---|
| 3,588,513 | 6/1971 | Takatsuki et al. | 356/430 |
| 3,806,009 | 4/1974 | Glaze, Jr. | 223/112 |
| 4,343,998 | 8/1982 | Mori | 250/559.42 |
| 4,541,351 | 9/1985 | Horita et al. | 223/43 |
| 4,656,463 | 4/1987 | Anders et al. | 340/572 |
| 4,744,035 | 5/1988 | Hashim | 356/431 |
| 4,748,334 | 5/1988 | Kobayashi et al. | 250/559.42 |
| 4,827,395 | 5/1989 | Anders et al. | 364/138 |
| 4,874,241 | 10/1989 | Egea et al. | 356/238 |
| 4,890,924 | 1/1990 | Beckstein | 356/238 |
| 5,133,198 | 7/1992 | Bachmann | 356/241 |
| 5,283,443 | 2/1994 | Norton-Wayne et al. | 250/559.42 |

FOREIGN PATENT DOCUMENTS

| | | | |
|---|---|---|---|
| 0 300 935 A1 | 1/1989 | European Pat. Off. | |
| 0529621 | 3/1993 | European Pat. Off. | |
| 1079585 | 12/1954 | France | |
| 72 21847 | 1/1973 | France | |
| 24 35 696 | 2/1976 | Germany | |
| 2552966 | 6/1977 | Germany | 356/237 |
| 3426056 | 1/1985 | Germany | |
| 57-146137 | 9/1982 | Japan | |
| 60-65173 | 4/1985 | Japan | |

OTHER PUBLICATIONS

Patent Abstracts of Japan, vol. 14, No. 325 (P–1075) 12 Jul. 1990 & JP,A,02 107951 (Mitsubishi Rayon Co Ltd.).
*Automated Garment Inspection Using Machine Vision,*. L. Norton–Wayne, Leicester Polytechnic, pp. 374–377 (No Date Available).
*The Automatic Inspection Myth or Reality?*, J. Yvain, L'Industrie Textile—N° 1199 Mai 1989, pp. 87–90 (also including translation).

(List continued on next page.)

*Primary Examiner*—Frank G. Font
*Assistant Examiner*—Jason D. Vierra Eisenberg
*Attorney, Agent, or Firm*—Bell Seltzer Intellectual Property Law Group of Alston & Bird LLP

[57] ABSTRACT

A garment inspecting and grading apparatus and methods of inspecting a garment are provided that preferably have a mounting member arranged to mount a garment thereon. A light emitter is positionally aligned closely adjacent the mounting member to emit light through a predetermined portion of a garment mounted thereon. A light detector is also positionally aligned with the light emitter to detect either the presence or absence of light traveling from the light emitter. A controller is positioned in electrical communication with the light detector and arranged to determine the presence and absence of defects in a predetermined portion of a garment responsive to electrical signals representative of the presence or absence of light received from the light detector. A grader and sorter are positioned downstream from the light emitter and the light detector for sorting an inspected garment into one of a plurality of predetermined quality groups.

34 Claims, 9 Drawing Sheets

OTHER PUBLICATIONS

*Pantyhose Inspecting Steam Boarding Packaging System,* Model TAS–15GL, Model THP–3GLW, Takatori Corporation, Japan, Jun. 1991.

*Pantyhose Inspecting Half–boarding Machine,* Model TAS–20GL, Takatori Corporation, Japan, May 1989.

*Continuous Pantyhose Boarding Machine,* Model TAS–150PO, Takatori Corporation, Sep. 1989.

*Continuous Socks Boarding Machine,* Model TAS–130MO, Takatori Corporation, Jun. 1987.

*Pantyhose Inspecting Half–Boarding Packaging System,* Model TAS–20GL, Model THP–3GL, Takatori Corporation, Jun. 1990.

*Continuous Socks Boarding Machine,* Model HAS–800, Takatori Corporation, Dec. 1989.

*Pantyhose Inspecting and Steam Boarding Machine,* Model TAS–15H, Takatori Corporation, Apr. 1994.

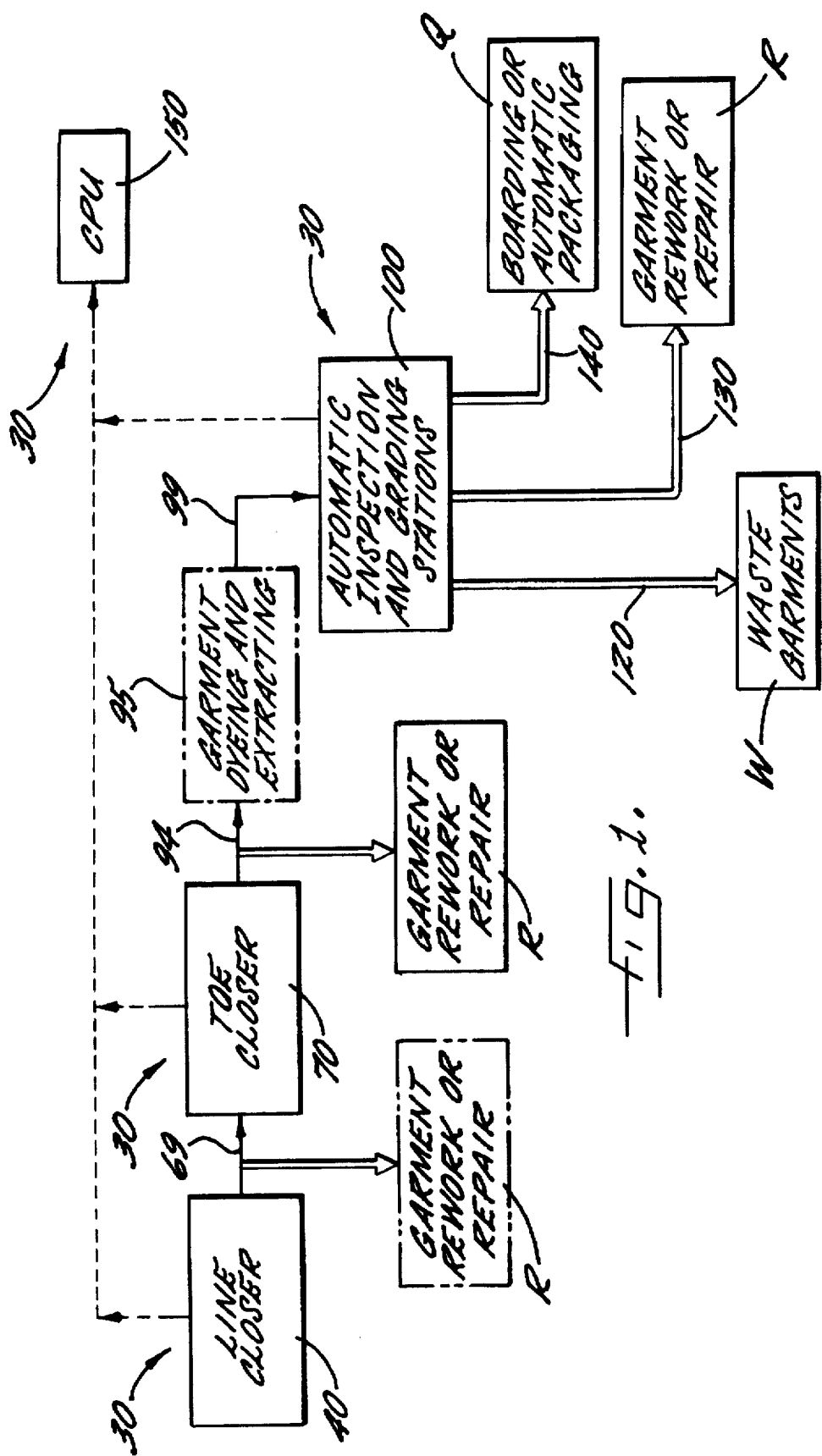

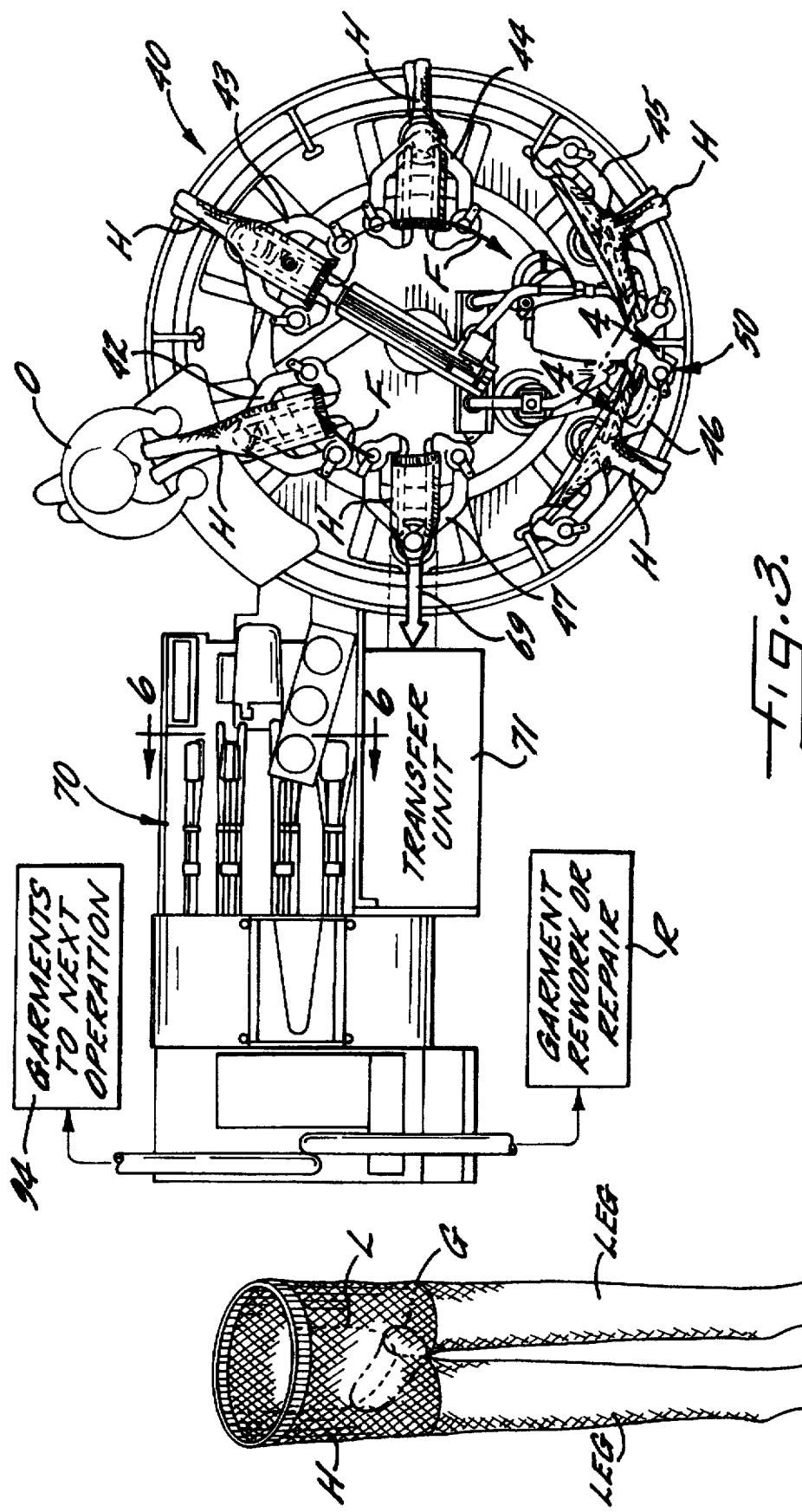

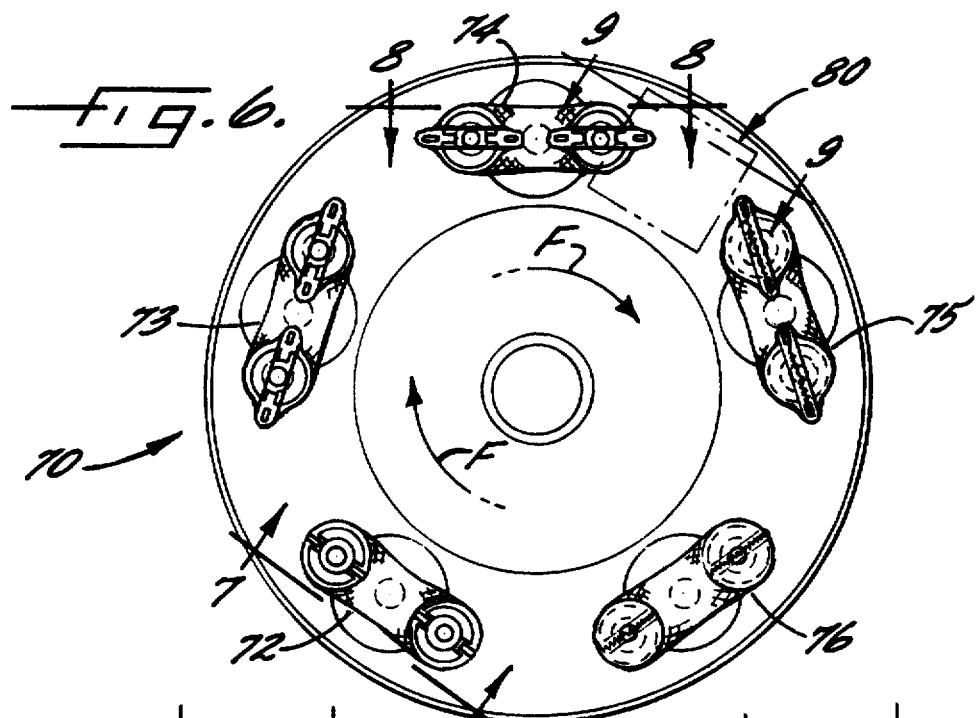
Fig. 6.
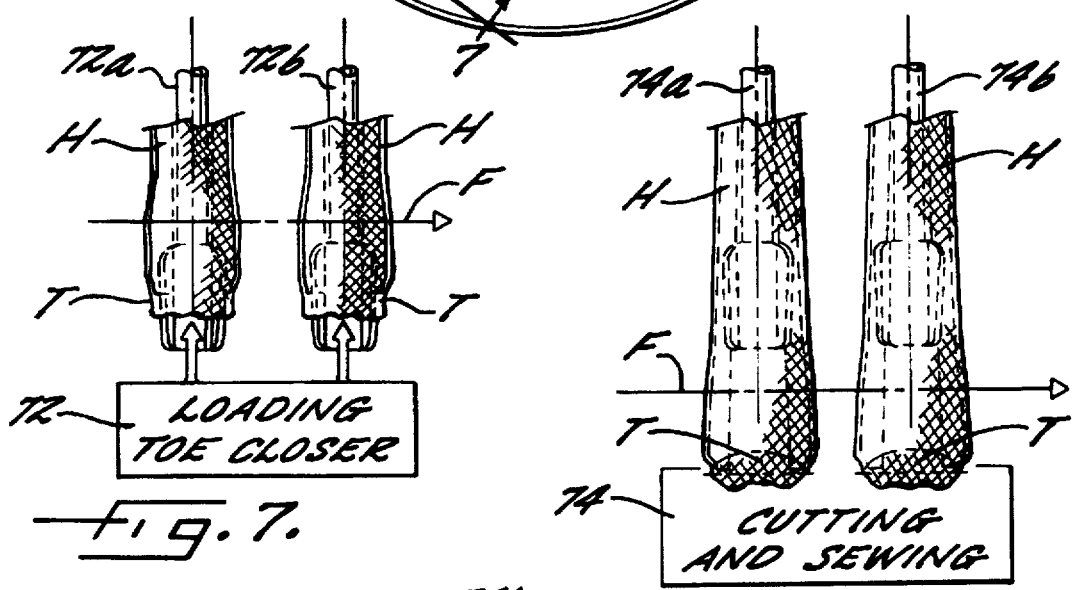
Fig. 7.
Fig. 8.
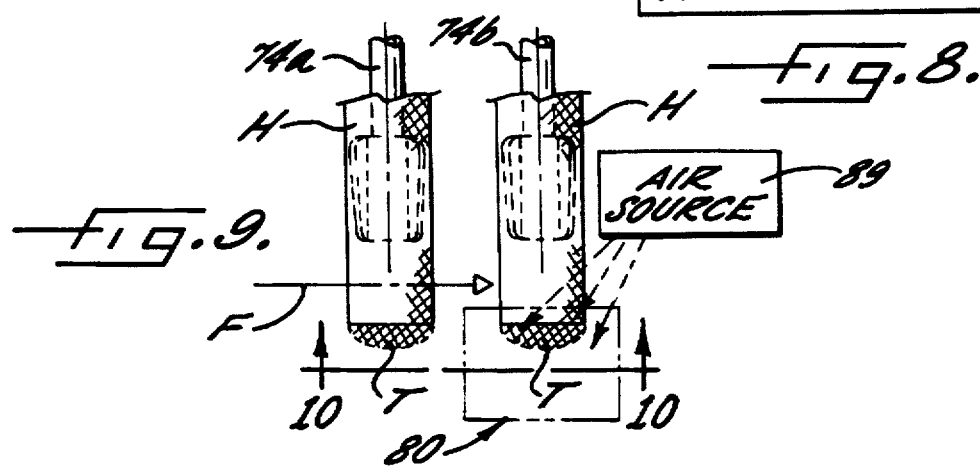
Fig. 9.

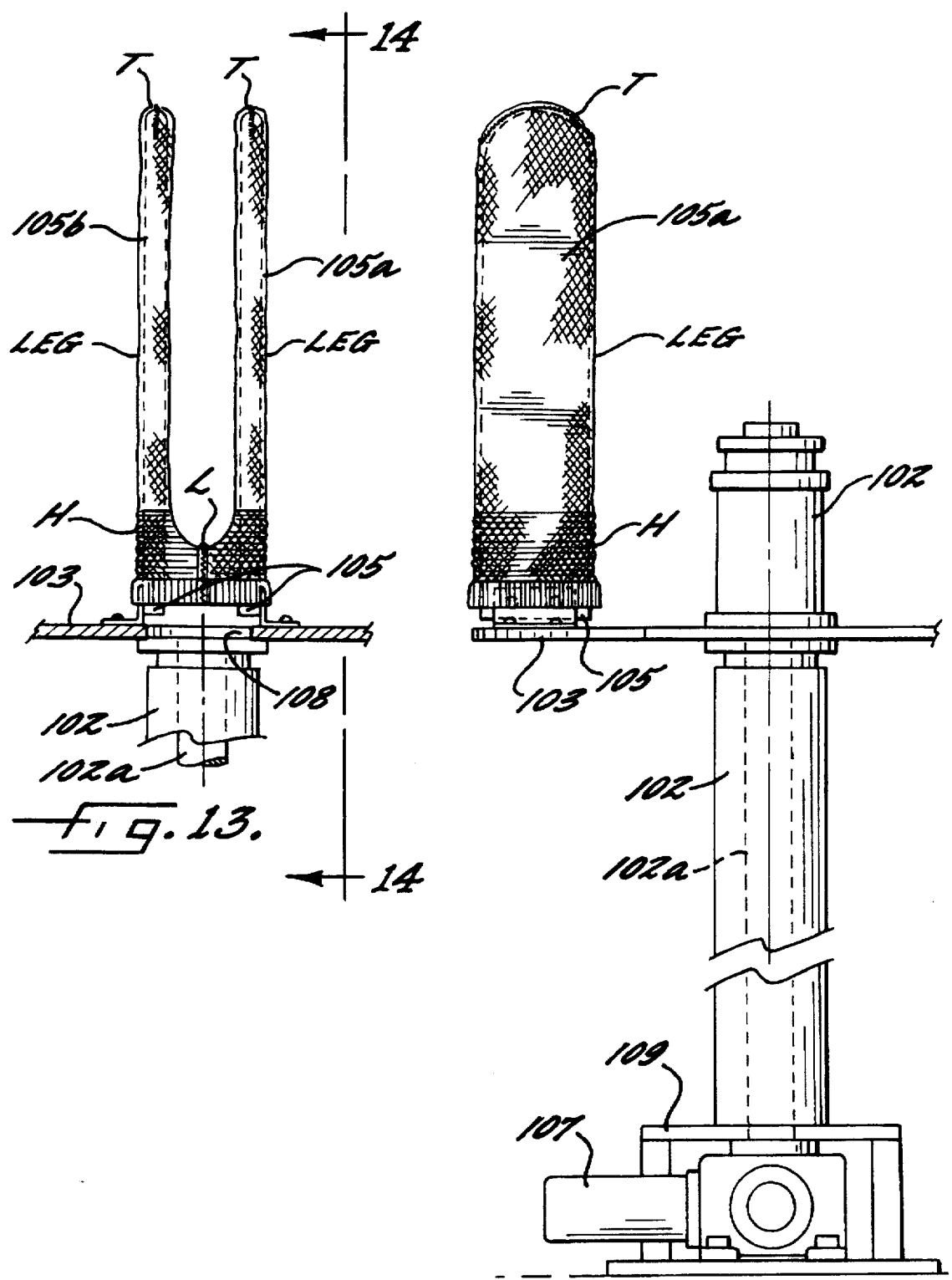

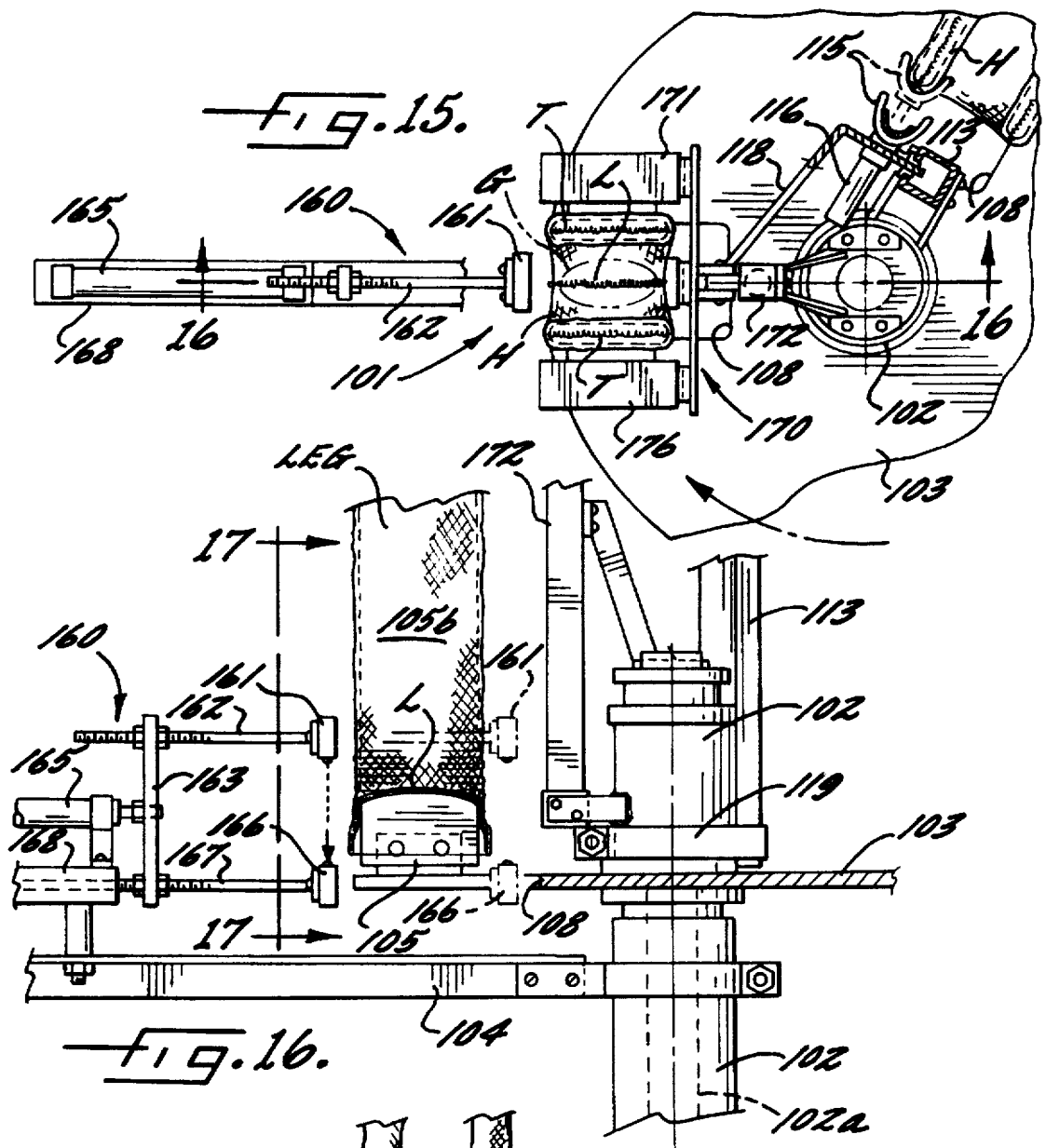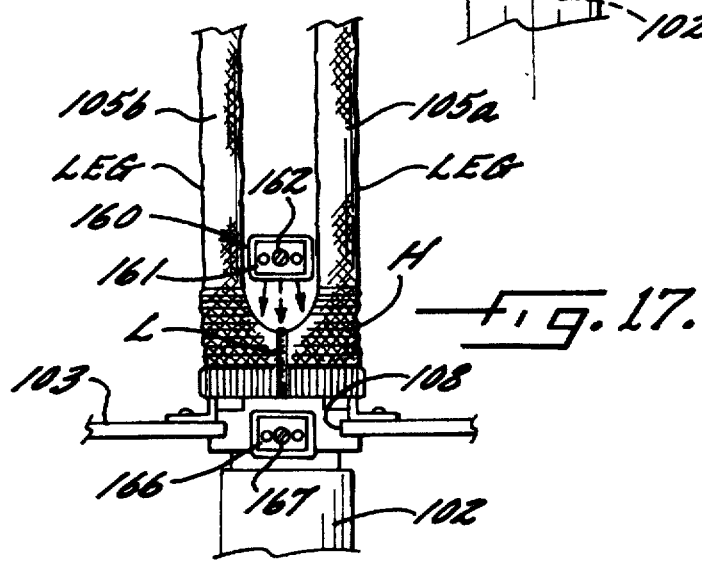

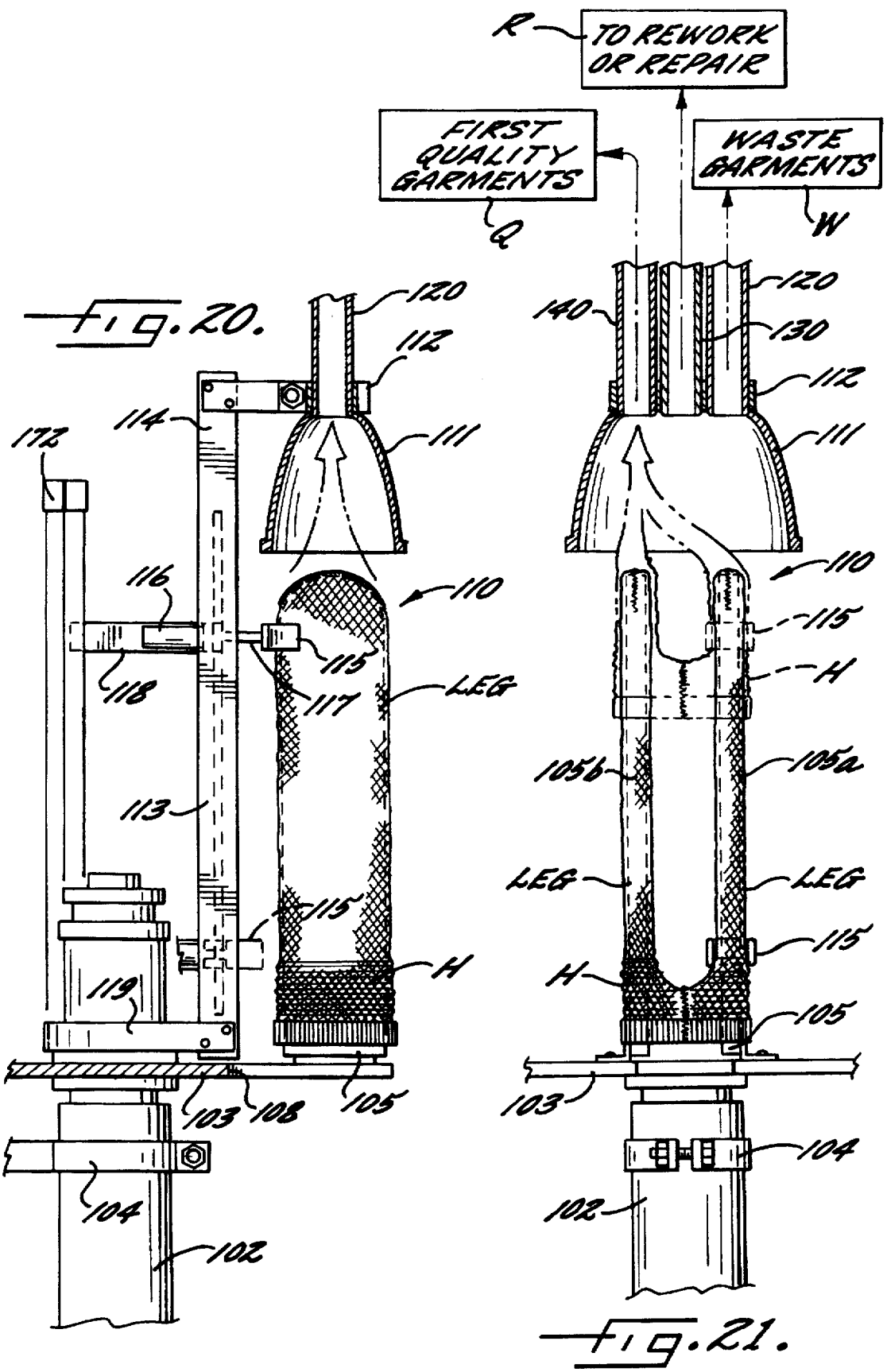

5,703,688

METHOD AND APPARATUS FOR INSPECTING AND GRADING GARMENTS

RELATED APPLICATIONS

This application is a continuation-in-part of U.S. patent application Ser. No. 08/371,810, filed on Jan. 12, 1995 now U.S. Pat. No. 5,497,235 which is hereby incorporated herein in its entirety by reference.

FIELD OF THE INVENTION

This invention relates to an inspecting and grading apparatus for garments and methods of inspecting garments such as during a manufacturing process.

BACKGROUND OF THE INVENTION

Over the years, the developments of various synthetic yarns have made possible the production of various knit garments such as tee-shirts, men and women's briefs, socks, and various other hosiery, e.g., knit leotards, pantyhose, tights, knee-highs, ankle socks, leggings, stockings. These developments, however, have also resulted in many changes in the methods and procedures employed in the production, packaging, and marketing of these garments.

The production difficulties precipitated by the popularity of the stretch synthetic yarns used in the production of garments also have been further magnified by the increased popularity of these various garments such as pantyhose and other stockings in general. Although the increased popularity has produced a need for increased automation in the production process and the accompanying reduction in cost, workable solutions to various problems have not been readily apparent and therefore have not been forthcoming.

In the manufacture of stretch pantyhose from synthetic yarns, for example, it is the conventional practice to knit the garment, either as a unitary structure (including the elastic waistband) or as separate components which are subsequently sewn together, from undyed yarns, and subsequently subjecting the undyed articles to shrinking and dyeing operations. The pantyhose therefore must be knitted, sewn, treated, inspected, transferred, and packaged in a manner that will not damage or unduly stretch the garment. Additionally, for example, the pantyhose may be flattened and shaped to such a degree as to be easily packaged so that the pantyhose provides an acceptable quality level and an attractive appearance to the purchaser when removed from the package.

One area in the production process where problems have developed over the years in the production of garments such as pantyhose is in the knitting and sewing operations. For example, operational troubles may often occur during knitting or sewing which results in defects, i.e., picks, faulty or incomplete stitching, in the garments and thereby may considerably degrade the commercial value of the article. If the defective garment reaches the market, it also may seriously blemish the reputation of the producer. Therefore, because these operations are imperfect, the knitted and/or sewn garment is required to be inspected and graded prior to packaging and shipment to retailers and consumers.

Conventionally, the inspection of garments such as pantyhose has been done by visual human inspection of the completed article prior to packaging. This manual visual inspection process, however, is often tedious, time consuming, and includes a varying degree of human judgment even for similar quality standards. Even a certain batch of garments, for example, may have a wide variation of quality levels depending on the worker that inspected the completed article. Some operations also employ more than one worker in a particular line operation to inspect the completed garment to ensure that an acceptable quality level is delivered to the retailers and consumers. Despite various inspecting tactics taken during the production process, the industry has been driven toward higher and more uniform production quality at a lower cost which manual labor often fails to provide.

Developments in the inspecting and grading process that have recently occurred have been targeted toward using video or charge coupled device ("CCD") cameras for inspecting a completed garment article. Examples of these video camera systems may be seen in European Published Application O-529-621 titled "Machine For The Quality Control of Knit Products, In Particular Fine-Gauge Pantyhose, Knee Socks, Ankle Socks, And The Like, As Well As Method For The Visual Inspection Of Knit Goods," Japanese Published Application 60-065-173 titled "Fibrous Product Checking Apparatus With Computer Providing Pictorial Information Using Two Television Cameras," and the articles "The Automatic Inspection, Myth Or Reality" by Jean-Michel Yvain in DML Engineering and "Automated Garment Inspection Using Machine Vision" by L. Norton-Wayne in Leicester Polytechnic.

Because the conventional video camera failed to provide the resolution and magnification necessary to accurately inspect a garment article for many types of defects, the industry responded with garment inspection systems having high resolution video or CCD cameras which are capable of providing a detailed visual image of the garment. These video and CCD cameras, however, are expensive and complex making them less attractive and not economically feasible to many producers of garments in the industry.

SUMMARY OF THE INVENTION

With the foregoing in mind, the present invention provides an accurate apparatus and method of inspecting and grading a garment such as during manufacturing to reduce labor costs and reduce the number of defective garments in a production process being sent to retailers and consumers. The present invention also advantageously provides an apparatus that determines an appropriate and a more uniform quality level of an inspected garment and that reduces human judgment in the production of a garment. The present invention further provides a relatively inexpensive and less complex inspecting and grading apparatus that determines a quality level of a garment without the necessity for use of cameras to visually assist in the inspection process.

More particularly, a garment inspecting and grading apparatus according to the present invention is provided that has means for mounting a garment. The mounting means is preferably formed of a translucent material. Optical inspecting means is positioned adjacent the mounting means for inspecting predetermined portions of a garment mounted on the mounting means. According to one embodiment, the optical inspecting means preferably includes at least one light emitter positionally aligned with a portion of the mounting means to emit light through a garment mounted thereon and at least one light detector positionally aligned with the at least one light emitter and the portion of the mounting means to detect either the presence or absence of light traveling from the light emitter and through predetermined portions of a garment mounted on the mounting means so that presence and absence of defects in a garment is thereby determined. Grading and sorting means is positioned downstream from the mounting means and the optical inspecting means and in electrical communication with the optical inspecting means for grading and sorting a garment responsive to the presence or absence of defects detected by the optical inspecting means.

Also, a garment inspecting apparatus for inspecting a stitch line of a hosiery garment such as a line of a gusset portion or a line of a toe portion of a leg of a hosiery garment is further provided according to the present invention. The garment inspecting apparatus preferably has a mounting member positioned to mount at least portions of a garment to be inspected and a shadow-forming member positioned adjacent the mounting member and a stitch line of a mounted garment. A light source is positioned to emit light along at least a portion of a stitch line of a garment so as to cause a shadow to be formed on the shadow-forming member. At least one detector preferably is positionally aligned with the shadow-forming member to detect the presence and absence of light positioned on the shadow-forming member so that presence and absence of defects in a stitch line of a garment are thereby determined.

Methods of inspecting a garment additionally are provided according to the present invention. A method of inspecting a garment preferably includes emitting light closely adjacent a portion of a stitch line of a garment mounted on a mounting member so as to form a shadow of the portion of the stitch line and detecting the presence and absence of defects in the portion of the stitch line responsive to a shadow representative of presence and absence of defects in the portion of the stitch line of a garment. The method may also include directing a gas toward a stitch line of a garment so as to cause a defect in the stitch line to be more easily recognized and grading a garment into at least one of a plurality of predetermined quality groups responsive to detecting the presence or absence of defects therein.

The present invention automates the inspecting and grading process for a garment so that a higher and more uniform degree of quality may be established with a system that manufacturers can afford. The inspecting and grading apparatus also reduces waste, for example, by determining whether a particular garment may be downgraded, reworked, or sold as a lower quality product which further saves the manufacturer time and money. Additionally, because the grading and/or sorting process can be controlled and monitored, the present invention also advantageously provides an apparatus that allows a manufacturer to track and monitor a source of defects as well as specific defective garments.

BRIEF DESCRIPTION OF THE DRAWINGS

Some of the objects and advantages of the present invention having been stated, others will become apparent as the description proceeds when taken in conjunction with the accompanying drawings in which:

FIG. 1 illustrates a schematic view of a garment inspecting and grading apparatus positioned in a garment production process according to an embodiment of the present invention;

FIG. 2 illustrates a perspective view of an embodiment of a garment in the form of knit pantyhose for inspecting and grading by an apparatus according to the present invention;

FIG. 3 illustrates a top plan view of a line closer and a toe closer including a garment inspecting and grading apparatus according to the present invention;

FIG. 6 schematically illustrates a front elevational view of a toe closer including a garment inspecting and grading apparatus according to the present invention;

FIG. 7 schematically illustrates a fragmentary top plan view of a garment in the form of legs of hosiery being mounted onto a toe closer which includes a garment inspecting and grading apparatus according to the present invention and taken along line 7—7 of FIG. 6;

FIG. 8 schematically illustrates a fragmentary top plan view of a garment in the form of legs of hosiery being cut and sewn by a toe closer including a garment inspecting and grading apparatus according to the present invention and taken along line 8—8 of FIG. 6;

FIG. 9 schematically illustrates a fragmentary top plan view of a garment in the form of legs of hosiery being inspected by a toe closer including a garment inspecting and grading apparatus according to the present invention and taken along line 9—9 of FIG. 6;

FIG. 13 illustrates a fragmentary front elevational view of a garment mounted on a boarding member of a garment inspecting and grading apparatus according to the present invention taken along line 13—13 of FIG. 12;

FIG. 14 illustrates a fragmentary side elevational view of a garment mounted on a boarding member of a garment inspecting and grading apparatus according to the present invention taken along line 14—14 of FIG. 13;

FIG. 15 illustrates a fragmentary top plan view of a garment inspecting and grading apparatus positioned to inspect a gusset portion and legs of a garment mounted thereon according to the present invention;

FIG. 16 illustrates a fragmentary sectional view of a garment inspecting and grading apparatus positioned to inspect a gusset portion and legs of a garment mounted thereon according to the present invention and taken along line 16—16 of FIG. 15;

FIG. 17 illustrates a fragmentary sectional view of a garment inspecting and grading apparatus positioned to inspect a gusset portion of a garment mounted thereon according to the present invention and taken along line 17—17 of FIG. 16;

FIG. 20 illustrates a fragmentary front elevational view of unloading of a garment by a garment inspecting and grading apparatus according to the present invention; and FIG. 21 schematically illustrates a side elevational view of unloading and sorting of a garment by a garment inspecting and grading apparatus according to the present invention.

DETAILED DESCRIPTION

Figure 4:
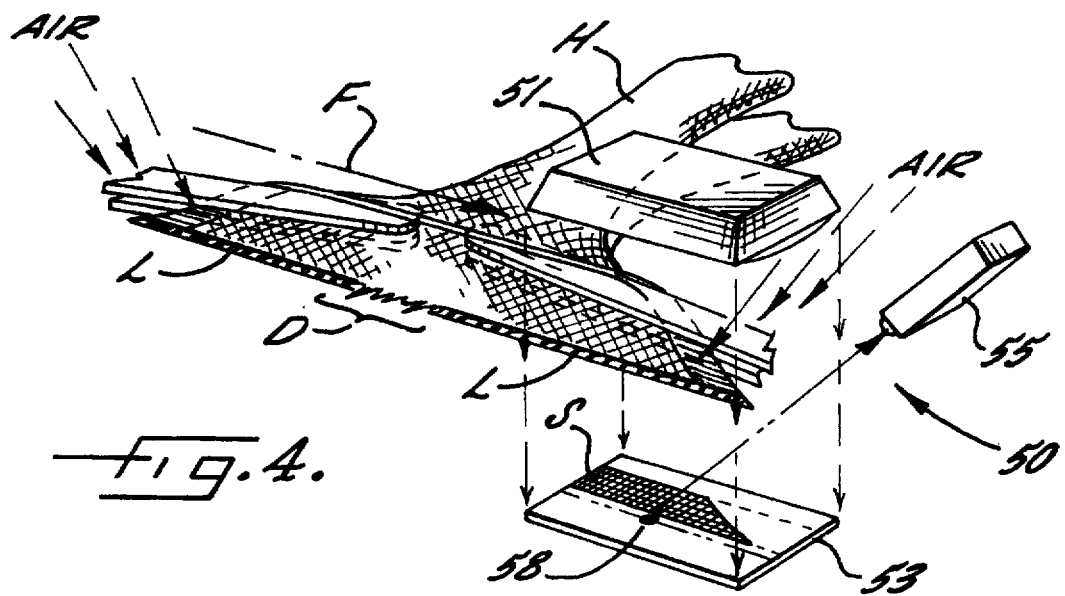
FIG. 4 schematically illustrates a perspective view of a garment inspecting and grading apparatus taken along line 4—4 of FIG. 3 and detecting the absence of defects according to the present invention.

The present invention will now be described more fully hereinafter with reference to the accompanying drawings in which preferred embodiments are shown. This invention, however, may be embodied in many different forms and should not be construed as limited to the illustrated embodiments set forth herein; rather, these embodiments are provided so that this disclosure will be thorough and complete and will fully convey the scope of the invention to those skilled in the art. Like numbers refer to like elements throughout.

FIG. 1 schematically illustrates examples of positional locations of at least one, and preferably more than one in a garment manufacturing system, garment inspecting and grading apparatus 30 according to the present invention. As illustrated, a garment inspecting and grading apparatus 30 may be positioned downstream from a garment dyeing and extracting apparatus 95 so that a garment H (see e.g., FIG. 2), such as knit leotards, pantyhose, tights, stockings, leggings, ankle socks, or the like, sometimes referred to generally as pantyhose, panty garments, or stockings, is transported to an automatic inspection and grading station 100 of the invention.

FIG. 2 illustrates an example of a garment in the form of pantyhose H to be inspected and graded by the apparatus 30 of the invention. The pantyhose H has a pair of legs LEG which each have a toe portion T at a lower end thereof. A panty portion P is secured to upper ends of the legs LEG. The panty portion P also preferably includes a waistband, a stitch gusset line L, and a gusset portion G as illustrated. The invention illustrates inspecting a stitch gusset line L, but as illustrated in FIGS. 13–21 the invention also includes inspecting other portions of the gusset G. Although the invention is illustrated as inspecting and grading a hosiery garment, the invention is also applicable to other types of garments such as knit shirts, underwear, and the like as well.

The inspection and grading station 100 in combination with a computer system and/or controller 150 having a central processing unit ("CPU") and means for sorting the inspected and graded garments 110 preferably together form an embodiment of a garment inspecting and grading apparatus 30 according to the invention. As illustrated, however, other embodiments of the present invention, for example, may be included in a line closer 40, a toe closer 70, or at other positions in a garment manufacturing process. One or more of these garment inspecting stations are preferably positioned in electrical communication with the CPU 150 for controlling the inspecting and grading process. Because the grading and/or sorting process can be controlled and monitored, for example, the present invention also advantageously provides an apparatus 30 that allows a manufacturer to track and monitor a source of defects as well as specific defective garments.

The inspected garments in such a system then can be graded and/or sorted, e.g., through tubing or other transport lines 120, 130, 140, into at least one of a plurality of predetermined quality groups such as waste W, rework or repair R, or first quality Q. First quality Q may also indicate that the garment H is to be passed to the next operation such as illustrated by system connections 69, 94, 99.

As illustrated in FIGS. 3, 6, and 13, an operator O may manually mount or a station may automatically mount a garment H onto one of a plurality of mounting members, e.g., 42, 72, 105 of the inspecting and grading stations 40, 70, 100. Each of the plurality of mounting members 42, 72, 105 is preferably formed of a pair of elongate and spaced-apart mounting forms or members, e.g., 72a, 72b, 105a, 105b. The garment H preferably is then inspected for defects D therein by an optical inspecting means, i.e., optical inspector, of the garment inspecting and grading apparatus 30 of the present invention. The inspected garment article H is then graded and sorted based on predetermined quality levels or groups and transported to either waste garments W, garment rework or repair R, i.e., seconds, irregulars, downgrades, or repairs, or boarding or automatic packaging, i.e., first quality Q. The seconds or downgrades, for example, may even have multiple levels of quality categories from top quality to varying degrees of lower quality and/or waste.

The controller 150 is positioned in electrical communication with the optical inspecting means, e.g., at least one detector 55, 85, 166, 173, 178, and is arranged to determine the presence and absence of defects D in a garment responsive to electrical signals representative of the presence or absence of light received from the at least one light detector 55, 85, 166, 173, 178 of the optical inspecting means. The controller 150 may form a part of or be positioned separately from a computer system having a CPU such as illustrated and may be a hardware and/or software implementation as understood by those skilled in the art.

The computer system 150 also preferably includes a memory device connected to the CPU, a keyboard connected to the CPU, and a display, such as a cathode ray tube ("CRT"), likewise connected to the CPU. The computer system 150, as illustrated in FIG. 1, provides operator O interaction, i.e., responsive to electrical command signals, and feedback with the inspecting and grading and sorting stations 40, 70, 100 of the apparatus 30. The computer system 150 further preferably provides means of recording or storing data related to defects in the inspected garments in a production process which, in turn, provides data for a manufacturer to use in measuring various production performance criteria, i.e., quality, throughput, number of reworks or downgrades, locate production problems, and the like. This data can be further processed by the computer system 150 for predetermined purposes as well as communicated to another data processing and/or displaying apparatus.

For example, if the inspected garment H is determined to be of first quality Q based upon predetermined quality standards or levels, then responsive to predetermined electrical signals received from the controller 150. The inspected garment H is preferably transported to the next operation, e.g., 71, 94, 140. For example, the inspected garment H can be transported to a transfer unit 71 or a mounting chamber via an auto-loader onto one of a plurality of empty mounting members, e.g., 72a, 72b, of a toe closer 70 positioned to receive the inspected garment H as best illustrated in FIGS. 6–7. The garment H may then be stitched along a toe portion thereof, further inspected, and transported to the next operation, which may by way of example be a garment dyeing and extracting process.

Figure 5:
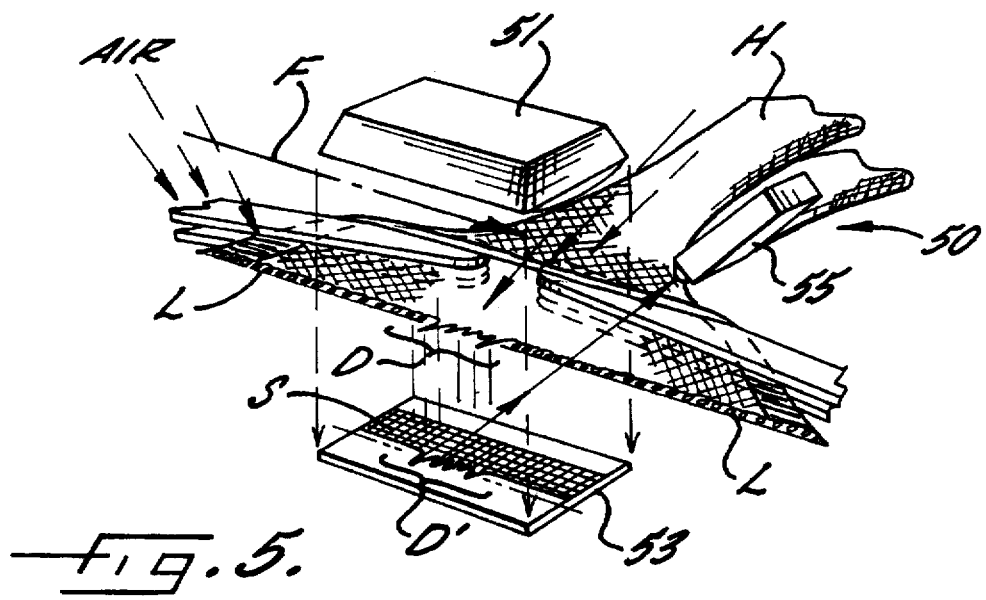
FIG. 5 schematically illustrates a perspective view of a garment inspecting and grading apparatus detecting the presence of defects according to the present invention.
Figure 10:
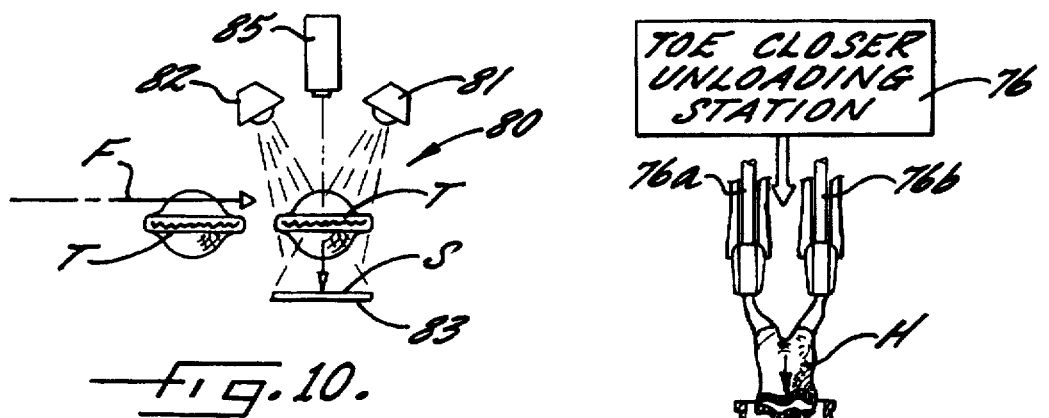
FIG. 10 schematically illustrates a front elevational view of a garment in the form of legs of hosiery being inspected by a toe closer including a garment inspecting and grading apparatus according to the present invention and taken along line 10—10 of FIG. 9.

FIGS. 3 and 6 respectively illustrate a line closer 40 and a toe closer 70 as embodiments of an inspecting and grading apparatus 30 and, more particularly, include means for sewing a line into a garment such as illustrated at the sewing positions 45, 74 according to the present invention. As understood by those skilled in the art, the line closer 40 preferably includes a plurality of operational positions illustrated by the direction process flow arrow F such as loading 42, cutting 43, adjusting or positioning 44, sewing 45, preparing to unload 46, and unloading 47. Preferably, stitch line inspecting means 50, as best illustrated in FIGS. 4–5, is positioned between the steps of sewing 45 and preparing to unload 46 as illustrated for inspecting a stitch line L of a garment H. Likewise, the toe closer 70, as understood by those skilled in the art, also preferably includes a plurality of operational positions such as loading 72 (see e.g., FIG. 7), adjusting or positioning 73, cutting and sewing 74 (see e.g., FIG. 8), preparing to unload 75, and unloading 76 (see e.g., FIG. 11) which are also illustrated by the directional process flow arrow F. Preferably, stitch line inspecting means 80, as best illustrated in FIGS. 9–10, is positioned between the steps of sewing 74 and preparing to unload 75 for inspecting a stitch line L of a toe portion of a garment H. The line closer 40, the toe closer 70, and the inspecting and grading station 100 are illustrated using a pair of hosiery legs LEG, but only one leg LEG may be mounted and inspected as well according to the present invention.

Figure 11:
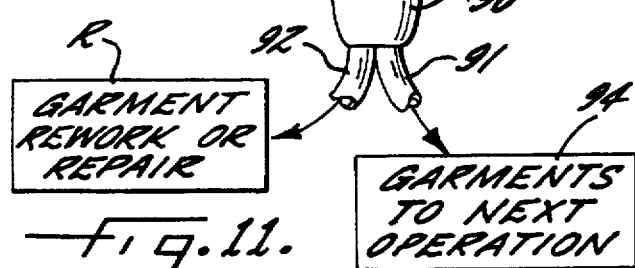
FIG. 11 schematically illustrates a fragmentary top plan view of a garment in the form of hosiery being graded and sorted by a garment inspecting and grading apparatus according to the present invention.

By way of example, as illustrated in FIGS. 4–5 and 9–10, the inspecting means 50, 80 of the line closer 50 and the toe closer 70, e.g., embodiments of a garment inspecting apparatus 30 preferably includes at least one mounting member, e.g., mounting members illustrated at 46 and/or 74a, 74b, positioned to mount at least portions of a garment to be inspected and a shadow-forming member 53, 83 positioned adjacent the mounting member and a stitch line L of a mounted garment H. The inspecting means 50, 80 also preferably includes at least one light source 51, 81, 82 positioned to emit light along at least a portion of stitch line L of a garment H so as to cause a shadow S to be formed on the shadow-forming member 53, 83. At least one detector, e.g., a Cutler-Hammer & Opcon distributed comet photoelectric detector, preferably is positionally aligned with the shadow-forming member 53, 83, and preferably aligned so as to form a defect detection window or area 58, to detect the presence and absence of light positioned on the shadow-forming member 53, 83 so that presence and absence of defects D in a stitch line L of a garment H, such as illustrated, are thereby determined. Additionally, both the toe closer 70 and the line closer 40 preferably include means, e.g., an air source 89, for directing gas toward the stitch line L to assist in the inspecting process by making it easier to detect a defect, e.g., by blowing air so as to separate portions of fabric, yarn, or thread after the cutting and sewing steps. After inspecting the stitch line L of the garment H, such as by the toe closer 70, and as illustrated in FIG. 11, the garment H can be unloaded by a vacuum or pneumatic assist device from the mounting members 76a, 76b through a first manifold 90 having at least two tubes or piping 91, 92 for transporting the inspected garment to either rework or repair R or the next first quality operation 94.

Figure 12:
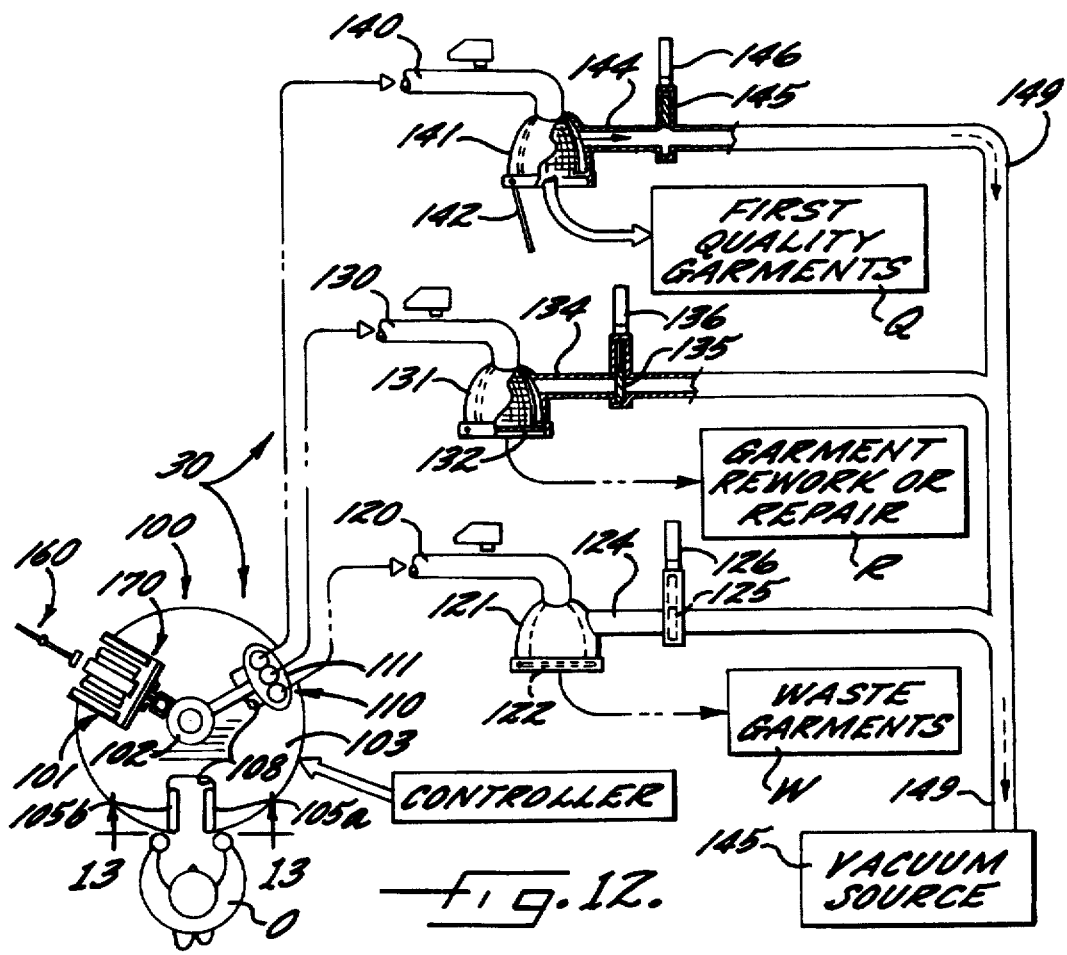
FIG. 12 schematically illustrates a fragmentary top plan view of a garment inspecting and grading apparatus according to the present invention.

As best illustrated in the top plan and schematic views of FIG. 12, a garment inspecting and grading apparatus 30 such as an inspecting and grading station 100 and means for sorting 110 according to the present invention preferably has a plurality of operational positions arranged for mounting, inspecting, unloading, and sorting a plurality of garments H thereon. As illustrated in FIGS. 12–21, the inspecting and grading station 100 preferably has a base member 102 illustrated in the form of a cylindrical mounting post. The base member 102 has upper and lower end portions. A lower base frame supports the base member 102 in an upright position and is formed by a pair of rectangular and spaced-apart lower plate members 109 and a plurality of leg members vertically extending therebetween. The base member 102 includes a base shaft 102a rotatably mounted to the lower plate or housing member, e.g., housing gears, etc., 109. The base shaft 102a is rotatably driven by a motor 107 and other associated drive means as understood by those skilled in the art. The upper end portion of the base member 102 preferably has an annular base plate 103 secured thereto for rotational movement about the upper end portion of the base member 102.

As illustrated in FIGS. 12–14, a plurality of pairs of elongate and spaced-apart board mounting members 105a, 105b preferably have lower portions 105 thereof mounted to respective mounting brackets secured to the base plate 103 so that rotation of the base plate 103 about the upper end portion of the base member 102 correspondingly rotates the board mounting members 105a, 105b. Each of the pair of elongate and spaced-apart board mounting members 105a, 105b extends upwardly from the base plate 103 secured to the upper end portion of the base member 102 and is respectively arranged to mount a pair of legs LEG of a garment such as pantyhose H thereon so that a gusset portion G of the pantyhose H extends between the pair of elongate and spaced-apart boarding members 105a, 105b and overlie a recess or cut-out portion 108 of the base plate 103. Each of the board mounting members 105a, 105b of this embodiment is also preferably formed of a translucent material so that during inspection light can pass through the board mounting member 105a, 105b and a predetermined portion of a garment mounted thereon.

As best illustrated in FIGS. 12–21, a garment inspecting and grading apparatus according to the present invention has optical inspecting means, i.e., optical inspector, which preferably includes a combination of a leg and/or toe inspector 170 (see FIGS. 15 and 18–19) and a gusset inspector 160 (see FIGS. 15–17) but may include only one or two of the leg/toe inspector 170 and the gusset inspector 160, e.g., depending on the production application. The leg/toe inspector 170 and the gusset inspector 160 may be mounted in various combinations or configurations to the base member 102 at either the same or different inspecting stations 100 according to the present invention. Preferably, however, the leg/toe inspector 170 and the gusset inspector 160 are mounted at the same inspecting station, and the toe portion of the leg/toe inspector 160 is preferably mounted so that a toe portion of a garment may also be inspected during the leg inspection process.

The leg/toe inspector 170 of the optical inspecting means has at least one light emitter 171, 176 positionally aligned with at least one, i.e., 112, of the board mounting members 105a, 105b and positioned to vertically travel generally parallel to a front surface of the board mounting member, e.g., 105a. The light emitter 171, 176 emits light onto and through the front surface of the board mounting member 105a and a portion of a toe T and/or a leg LEG of pantyhose H when mounted thereon.

The light emitter 171, 176 of the leg inspector 160 preferably has a housing having a light emitting diode positioned therein and a plurality of optical fibers optically aligned with the light emitting diode. The optical fibers are arranged to transmit light received from the light emitting diode to a portion of leg LEG of a garment H mounted on the board mounting member 105a. The light from the optical fibers preferably travels through an elongate slit formed in an end of the housing and is transmitted toward and through the board mounting member 105a and a portion of the leg LEG of the garment H mounted thereon.

The leg/toe inspector 160 of the optical inspecting means also preferably includes at least one light detector 173, 178 positionally aligned with the light emitter 171, 176 and at least one of the plurality of board mounting members 105a, 105b and positioned to vertically travel generally parallel to a back surface of at least one elongate board mounting member 105a. The light detector 173, 178 detects the presence and absence of light traveling from the light emitter 171, 176 and through the board mounting member 105a, 105b and the portion of the pantyhose H mounted thereon, as illustrated by the directional arrows of FIG. 19, so that presence and absence of defects D, such as picks of various sizes, in a garment such as pantyhose H mounted on the board mounting member 105 are thereby determined.

The light detectors 173, 178 likewise preferably have a housing and an optical receiver positioned within the housing. A plurality of optical fibers are arranged to receive light transmitted from the light emitters 171, 176. The optical fibers preferably are arranged along a corresponding elongate slit in an end portion of the housing.

More particularly as illustrated in the previous copending patent application by the same inventor which previously has been incorporated herein by reference, for example, the absence of light received in a portion of light detector 173 preferably corresponds to a defect D or pick detected in a portion of the leg LEG of the garment article H. The presence of light accordingly corresponds to either no defect D detected or a defect D or pick of such a small size as to be acceptable, not noticeable, or otherwise prevent the garment article H from obtaining a predetermined quality level. Because the light emitter 171 and the light detector 173 preferably have an array of optical fibers linearly disposed across corresponding horizontal slits, the presence or absence of light is readily detected by the leg/toe inspector 170. It will also be understood by those skilled in the art that various other arrays, such as a plurality of linearly disposed individual light emitting diodes and/or optical receivers, or other stacked or vertically orientations also are taught according to the leg/toe inspector 170 of the invention.

The light emitters 171, 176 and the light detectors 173, 178 of the leg/toe inspector 170, as well as those of the gusset inspector 160 further described herein, preferably are each respectively in electrical communication with and connected to the controller 150 such as by electrical cable and connectors. The light emitters 161, 171, 176 and the light detectors 166, 173, 178 of the optical inspecting means forming the leg/toe inspector 170 and the gusset inspector 160 are preferably like the 500 series DC scanners, i.e., SM53E and SM53R, manufactured by Banner Engineering Corporation of Minneapolis, Minn. and also preferably include Banner AC-coupled amplifiers or similar circuitry positioned in electrical communication with the light emitters and the light detectors as understood by those skilled in the art.

The light emitters 171, 176 and light detectors 173, 178 corresponding to each board mounting member 105a, 105b of the apparatus 30 further are preferably mounted in a spaced-apart relation by respective mounting brackets secured to the respective housings to a mounting plate 179. The mounting plate 179 is secured to a coupling 118 which is slidably positioned along a vertically-extending mounting member 172 secured to and extending generally parallel to the base member 102. The vertically-extending mounting member 172a is secured to the base member 102 by lower and upper mounting brackets secured to respective ends thereof.

Figure 18:
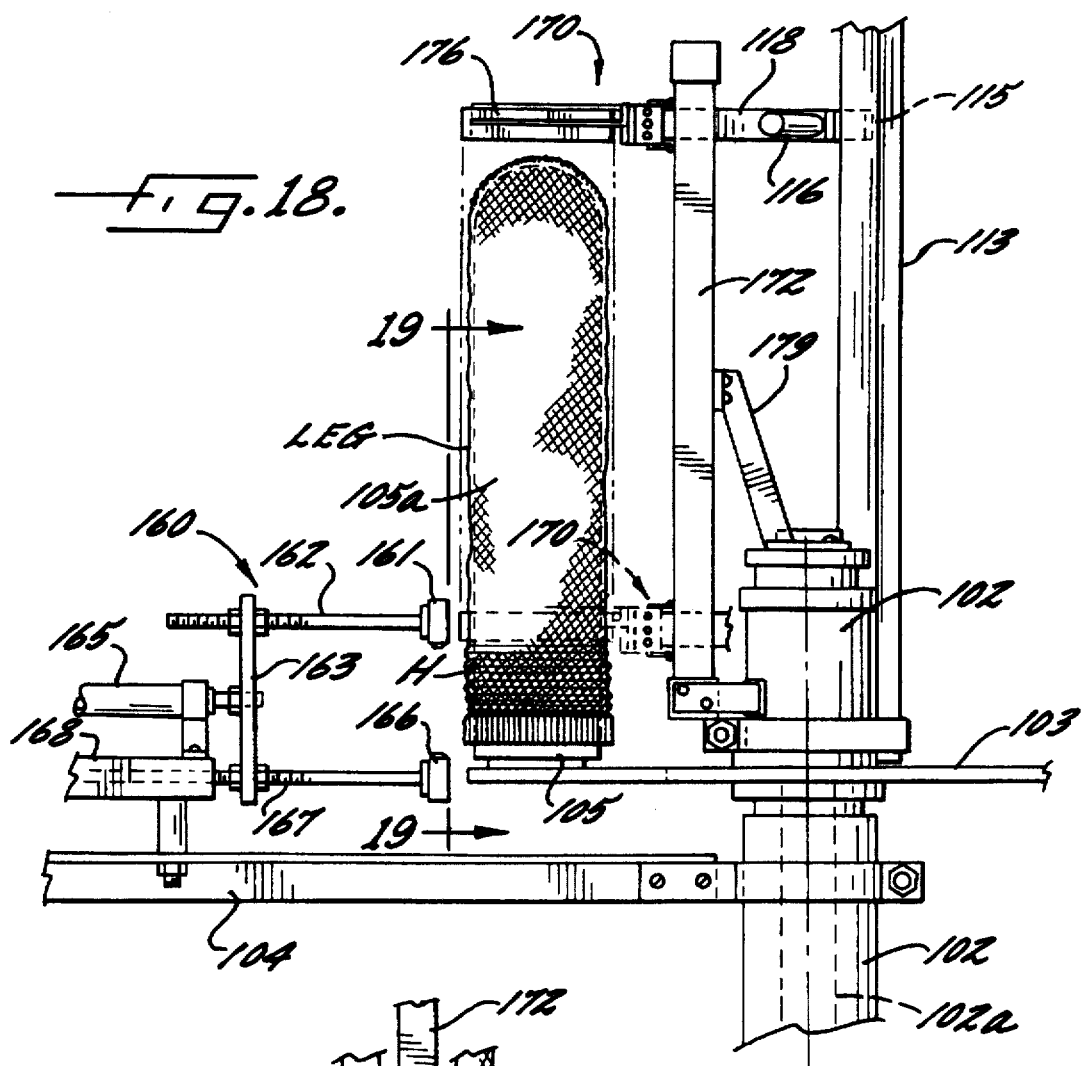
FIG. 18 illustrates a fragmentary front elevational view of a garment inspecting and grading apparatus positioned to inspect legs and a gusset of a garment mounted thereon according to the present invention.
Figure 19:
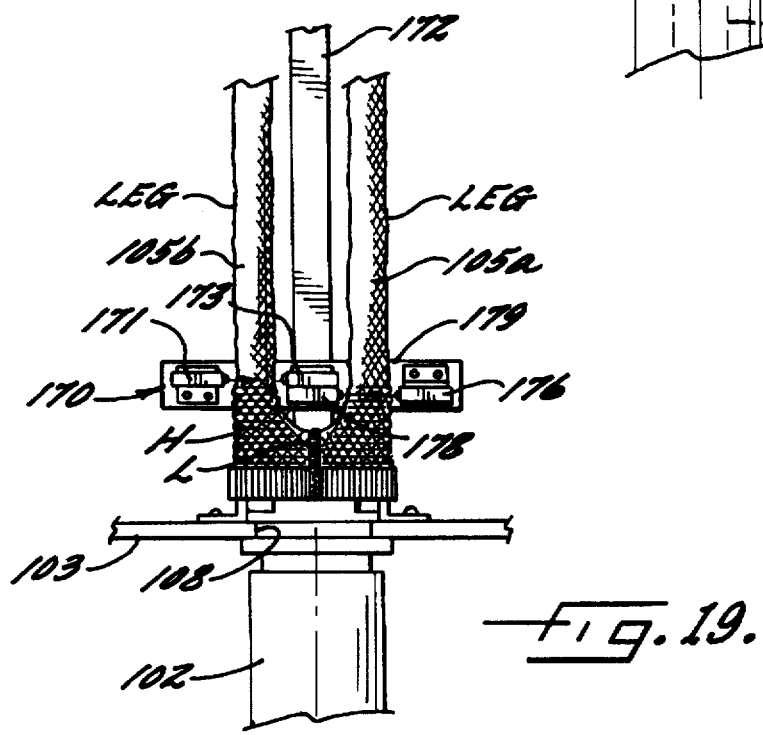
FIG. 19 illustrates a fragmentary side elevational view of a garment inspecting and grading apparatus inspecting legs of hosiery according to the present invention and taken along line 19—19 of FIG. 18.

Also, as illustrated in FIGS. 18 and 19, each board mounting member 105a, 105b preferably has at least one light emitter 171 and a corresponding at least one light detector 173 mounted for detecting defects in the leg LEG of the garment article H. The mounting arrangement of the light emitter 171 and light detector 173 respectively may include more than emitter and/or detector. As also understood by those skilled in the art, these emitters and detectors may also be customized for sizing and positioning for specific applications according to the garment inspecting and grading apparatus of the present invention.

The mounting arrangement of the leg inspector 170 as illustrated provides a scanning-type motion as the light emitters 171, 176 and the light detectors 173, 178 vertically travel up and down the leg LEG of the garment H as illustrated by the phantom lines in FIG. 18. The light detectors 173, 178 preferably are mounted closely adjacent each other on the mounting plate 179 and extend between the pair of elongate and spaced-apart board mounting members 105a, 105b.

As best illustrated in FIGS. 15–17, the optical inspecting means also preferably includes a gusset inspector 160 having at least one light emitter 161 arranged to emit light through a gusset portion G extending between a pair of legs LEG of pantyhose H mounted on the pair of board mounting members 105a, 105b. At least one light detector 166 is positionally aligned with the light emitter 161 and arranged to detect light traveling from the light emitter 161 and through a gusset portion G of the pantyhose H so that presence and absence of defects D, such as holes, faulty or incomplete stitching, in the gusset portion G are thereby determined. The gusset inspector 160 is also preferably positioned in electrical communication with the controller 150.

For example, the presence of light received in a portion of the light detector 166 preferably corresponds to a defect D or hole detected in the gusset portion G of the garment article H. The absence of light accordingly corresponds to either no defect D detected or a defect D or hole of such a small size as to be acceptable, not noticeable, or otherwise prevent the garment article H from obtaining a predetermined quality level. Because the light emitter 161 and the light detector 166, like those of the leg/toe inspector 170, preferably have an array of optical fibers linearly disposed across corresponding horizontal slits positioned in a housing thereof, the presence or absence of light is readily detected by the gusset inspector 160. It will also be understood by those skilled in the art that various other arrays, such as a plurality of linearly disposed individual light emitting diodes and/or optical receivers, or other stacked or vertical orientations also are taught according to the gusset inspector 160 of the optical inspecting means of the present invention.

The light emitter 161 and the light detector 166 of the gusset inspector 160, as best illustrated in FIGS. 15–16, are preferably mounted on respective horizontally extending shaft members 162, 167 which extend and retract into respective piston or shaft housings 165, 168 and are secured to a vertically extending plate member 163 to thereby form a generally C-shape configuration. The piston housings 165, 168 are secured to a mounting plate 104 which, in turn, is secured to the base member 102 so that the inspector 160 provides a generally-horizontal scan of the gusset portion G of the pantyhose H.

As best illustrated in FIGS. 12 and 20–21, the garment inspecting and grading apparatus 30 has grading and sorting means 110 positioned downstream from the optical inspecting means for grading and sorting inspected pantyhose H into predetermined quality groups. The grading and sorting means 110 preferably includes means positioned adjacent to at least one boarding member 105a, 105b for removing and receiving pantyhose H mounted thereon. The removing and receiving means preferably includes a manifold 111 positioned to receive an inspected garment article H. The manifold 111 preferably includes a cavity or chamber having a lower opening positioned closely adjacent the pair of boarding members 105a, 105b so that the entire garment H may be received therein. A plurality of tubes 120, 130, 140 is connected to the manifold 111 along an upper end portion thereof and is arranged to sort an inspected garment article H into various quality levels or groups responsive to electrical signals received from the controller 150. The plurality of tubes 120, 130, 140 preferably comprise three tubes as illustrated, but may comprise two or more, i.e., five, six, seven, etc., tubes for various quality categories according to the present invention.

A pneumatic device 145 such as a vacuum blower or source, preferably a high cubic feet per minute vacuum blower, is connected to the tubes 120, 130, 140 and preferably arranged to provide a vacuum-type removal of an inspected garment article H mounted on the boarding members 105a, 105b through a main tube 149 and a plurality of respective tubes 124, 134, 144 which respectively are connected to the first plurality of tubes 120, 130, 140 at respective discharge gates 121, 131, 141. Each of the discharge gates 121, 131, 141 also have a pivoting gate member 122, 132, 142 which pivotally opens to discharge the inspected and graded garment article H into a corresponding quality group, i.e., first quality Q, rework or repair R, waste W, as illustrated by the arrows.

Based on the predetermined quality level detected by the optical inspecting means, one of the tubes 124, 134, 144 corresponding to that quality level, i.e., first quality Q, rework or repairs R, waste W, will then have vacuum pressure applied thereto responsive to opening one of a plurality of corresponding valve gates 125, 135, 145 connected to the tubes 124, 134, 144. The valve gates 125, 135, 145 are also electrically connected to the controller 150 so that the removed garment article H received into the cavity of the manifold 111 is responsively drawn and sorted into the appropriate tube 120, 130, 140 and to the corresponding discharge gate 121, 131, 141. Each of the valve gates 125, 135, 145 has a corresponding valve member 126, 136, 146 which opens or shuts responsive to electrical signals representative of commands received from the controller 150 to either prevent or allow vacuum pressure from the vacuum source 145 to pass through the corresponding tube 120, 130, 140 directly connected to the manifold 111.

As the inspected garment article H passes through the selected tube 120, 130, 140 it preferably is also counted by a corresponding counter as illustrated connected to the selected tube 120, 130, 140. The sorting and counting of the grading and sorting means 110 is an example of a method and the apparatus capability to further provide quality control feedback to the operator O on the number and quality of garments inspected. The removal of the inspected garment H may be further assisted by a retractable and extendable removing U-shaped member 115 mounted to the frame 114 of the station 100 and which travels upwardly and downwardly corresponding to the scan of the leg/toe inspector 170 at an inspecting position 101 as illustrated.

Additionally, as illustrated in FIGS. 1–21, methods of inspecting, grading, and sorting a garment additionally are provided according to the present invention. A method of inspecting a garment preferably includes emitting light closely adjacent a portion of a stitch line of a garment mounted on a mounting member so as to form a shadow of the portion of the stitch line and detecting the presence and absence of defects in the portion of the stitch line responsive to a shadow representative of presence and absence of defects in the portion of the stitch line of a garment. The method may also include directing a gas toward a stitch line of a garment so as to cause a defect in the stitch line to be more easily recognized and grading a garment into at least one of a plurality of predetermined quality groups responsive to detecting the presence or absence of defects therein.

As described herein, the present invention automates the inspecting and grading process for a garment so that a higher and more uniform degree of quality may be established with a system that manufacturers can afford. The inspecting and grading apparatus also reduces waste, for example, by determining whether a particular garment may be downgraded, reworked, or sold as a lower quality product which further saves the manufacturer time and money. Additionally, because the grading and/or sorting process can be controlled and monitored, the present invention also advantageously provides an apparatus that allows a manufacturer to track and monitor a source of defects as well as specific defective garments.

Although the invention is particularly well adapted to the processing of garments such as knit leotards, pantyhose, tights, stockings, or the like, sometimes referred to above generally as pantyhose or panty garments, the invention is not limited to use in the production of such garments H, but rather may have general application in the production, handling, and packaging of various articles. Thus, although the invention has been described more particularly herein with specific reference to stockings and pantyhose H, this reference is for convenience of description of a preferred embodiment only, and it is understood that the invention is not so limited.

In the drawings and specification, there have been disclosed a typical preferred embodiment of the invention, and although specific terms are employed, the terms are used in a descriptive sense only and not for purposes of limitation. The invention has been described in considerable detail with specific reference to this illustrated embodiment. It will be apparent, however, that various modifications and changes can be made within the spirit and scope of the invention as described in the foregoing specification and as defined in the appended claims.

That which is claimed:

1. A garment inspecting and grading apparatus for inspecting a garment, the apparatus comprising:

means for mounting a garment thereon, said mounting means being formed of translucent material;

optical inspecting means positioned adjacent said mounting means for inspecting predetermined portions of a garment mounted on said mounting means, said optical inspecting means including at least one light emitter positionally aligned with a portion of said mounting means to emit light through a predetermined portion of a garment mounted thereon and at least one light detector positionally aligned with said at least one light emitter and the portion of said mounting means to detect either the presence or absence of light traveling from said light emitter and through the predetermined portion of a garment article mounted on said mounting means so that presence and absence of defects in a garment are thereby determined; and means positioned downstream from said mounting means and said optical inspecting means and in electrical communication with said optical inspecting means for grading and sorting a garment into one of a plurality of predetermined quality groups responsive to the presence or absence of defects detected by said optical inspecting means.

2. A garment inspecting and grading apparatus as defined by claim 1, wherein said grading and sorting means includes means positioned adjacent said mounting means for removing and receiving an inspected and graded garment from said mounting means.

3. A garment inspecting and grading apparatus as defined by claim 2, further comprising means positioned downstream from said grading and sorting means for receiving and packaging an inspected and graded garment.

4. A garment inspecting and grading apparatus as defined by claim 2, further comprising means in electrical communication with said optical inspecting means and said grading and sorting means for controlling said grading and sorting means responsive to electrical signals received from said optical inspecting means.

5. A garment inspecting and grading apparatus as defined by claim 4, wherein said mounting means comprises at least one elongate boarding member arranged to mount a leg of a garment thereon, and wherein said at least one light emitter and said at least one light detector of said optical inspecting means are mounted for reciprocatory movement upwardly and downwardly along said mounting means.

6. A garment inspecting and grading apparatus as defined by claim 4, wherein said at least one light emitter and said at least one light detector of said optical inspecting means respectively comprise at least a first light emitter and at least a first light detector arranged to inspect at least a first predetermined portion of a garment.

7. A garment inspecting and grading apparatus as defined by claim 6, wherein said mounting means comprises a pair of elongate and spaced-apart boarding members respectively arranged to mount a pair of legs of a garment thereon, and wherein said at least a first light emitter and said at least a first light detector of said optical inspecting means are mounted for reciprocatory movement upwardly and downwardly along at least one of said elongate boarding members.

8. A garment inspecting and grading apparatus as defined by claim 1, further comprising means in electrical communication with said at least one light detector for storing data representative of defects in a garment.

9. A garment inspecting apparatus for inspecting a garment, the apparatus comprising:

a mounting member formed of translucent material arranged to mount at least a portion of a garment thereon;

a light emitter positionally aligned closely adjacent said boarding member to emit light through a predetermined portion of a garment mounted thereon;

a light detector positionally aligned with said light emitter to detect either the presence or absence of light traveling from said light emitter;

a controller in electrical communication with said light detector and arranged to determine the presence and absence of defects in a predetermined portion of a garment responsive to electrical signals representative of the presence or absence of light received from said light detector; and means positioned downstream from said light emitter and said light detector for sorting an inspected garment into one of a plurality of predetermined quality groups.

10. A garment inspecting apparatus as defined by claim 9, wherein said sorting means includes means positioned adjacent said mounting member for removing and receiving an inspected garment therefrom, said removing and receiving means comprising a manifold positioned to received an inspected garment therein, a plurality of tubes connected to said manifold and arranged to sort an inspected garment responsive to said controller, and a pneumatic device connected to said tubes and arranged to provide a pressurized removal of an inspected garment article mounted on said mounting member.

11. A garment inspecting and grading apparatus for inspecting a hosiery garment, the apparatus comprising:

a base;

a plurality of mounting members rotatably connected to said base for mounting at least leg and gusset portions of a hosiery garment thereon;

at least one light emitter positionally aligned closely adjacent said mounting member and mounted to said base for emitting light through a predetermined portion of a leg of a hosiery garment during reciprocal and vertical movement along a leg of a hosiery garment mounted on at least one of said plurality of mounting members;

at least one light detector positionally aligned with said at least one light emitter for detecting either the presence or absence of light traveling from said at least one light emitter;

a controller in electrical communication with said at least one light detector and arranged to determine the presence and absence of defects in a predetermined portion of a garment responsive to electrical signals representative of the presence or absence of light received from said light detector; and means positioned downstream from said light emitter and said light detector for sorting an inspected garment into one of a plurality of predetermined quality groups.

12. A garment inspecting apparatus as defined by claim 11, wherein said sorting means includes means positioned adjacent one of said plurality of mounting members for removing and receiving an inspected hosiery garment therefrom, said removing and receiving means comprising a manifold positioned to received an inspected garment therein, a plurality of tubes connected to said manifold and arranged to sort an inspected garment responsive to said controller, and a pneumatic device connected to said tubes and arranged to provide a pressurized removal of an inspected hosiery garment mounted on said mounting member.

13. A garment inspecting and grading apparatus as defined in claim 12, wherein said plurality of mounting members comprises at least three spaced-apart mounting members rotatably connected to said base, said plurality of mounting members being respectively mounted at predetermined angles from each other so that a first position of said at least three mounting members is a position for loading a hosiery garment thereon, a second position is a position for inspecting and grading a loaded hosiery garment, and a third position is a position for unloading and sorting a hosiery garment.

14. A garment inspecting apparatus for inspecting a stitch line of a garment, the garment inspecting apparatus comprising:

a mounting member positioned to mount at least portions of a garment to be inspected;

a shadow-forming member positioned adjacent said mounting member and a stitch line of a mounted garment;

a light source positioned to emit light along at least a portion of stitch line of a garment so as to cause a shadow to be formed on said shadow-forming member; and at least one detector positionally aligned with said shadow-forming member to detect the presence and absence of light positioned on said shadow-forming member so that presence and absence of defects in a stitch line of a garment are thereby determined.

15. A garment inspecting apparatus as defined in claim 14, further comprising means positioned downstream from said mounting member and in electrical communication with said at least one detector for grading and sorting a garment responsive to the presence or absence of defects detected by said at least one detector.

16. A garment inspecting apparatus as defined by claim 15, further comprising means in electrical communication with said at least one detector and said grading and sorting means for controlling said grading and sorting means responsive to electrical signals received from said at least one detector.

17. A garment inspecting apparatus as defined in claim 14, further comprising means positionally aligned closely adjacent said mounting member for sewing a stitch line in a garment.

18. A garment inspecting apparatus as defined in claim 14, further comprising means positioned adjacent said at least one detector for directing a gas toward a stitch line of a garment so as to cause a defect in a stitch line to be more easily recognized by said at least one detector.

19. A garment inspecting apparatus for inspecting a stitch line of a hosiery garment, the garment inspecting apparatus comprising:

a pair of elongate and spaced-apart boarding members arranged to mount a pair of legs of a hosiery garment thereon;

means positioned closely adjacent said pair of mounting members for sewing a stitch line in legs of a hosiery garment mounted on said pair of boarding members;

a shadow-forming board member positioned adjacent a stitch line of a hosiery garment;

a light source positioned to emit light along at least a portion of a stitch line of a hosiery garment so as to cause a shadow to be formed on said shadow-forming board member; and a light detector positionally aligned with said board member to detect the presence and absence of defects in a stitch line responsive to a shadow formed on said board member so that presence and absence of defects in a stitch line of a hosiery garment are thereby determined.

20. A garment inspecting apparatus as defined in claim 19, further comprising means positioned downstream from said pair of mounting members and in electrical communication with said at least one detector for grading and sorting a garment responsive to the presence or absence of defects detected by said at least one detector.

21. A garment inspecting apparatus as defined by claim 20, further comprising means in electrical communication with said at least one detector and said grading and sorting means for controlling said grading and sorting means responsive to electrical signals received from said at least one detector.

22. A garment inspecting apparatus as defined in claim 21, further comprising means positionally aligned closely adjacent said mounting member for sewing a stitch line in a hosiery garment.

23. A garment inspecting apparatus as defined in claim 22, further comprising means positioned adjacent at least one detector for directing a gas toward a stitch line of a garment so as to cause a defect in a stitch line to be more easily recognized by said at least one detector.

24. A garment sewing and inspecting apparatus for inspecting a toe portion of a leg of a hosiery garment, the garment inspecting apparatus comprising:

at least one elongate mounting member arranged to mount a toe portion of a leg of a hosiery garment thereon;

means for sewing a stitch line into a toe portion of a leg of a hosiery garment;

a shadow-forming board member positioned adjacent a stitched toe line of a hosiery garment;

a light source positioned to emit light along at least a portion of a stitched toe line of a hosiery garment so as to cause a shadow to be formed on said board member; and a light detector positionally aligned with said board member to detect the presence and absence of defects in a stitched toe line responsive to a shadow formed on said board member so that presence and absence of defects in a stitched toe line of a hosiery garment are thereby determined.

25. A garment inspecting apparatus as defined in claim 24, further comprising means positioned downstream from said pair of mounting members and in electrical communication with said at least one detector for grading and sorting a garment responsive to the presence or absence of defects detected by said at least one detector.

26. A garment inspecting apparatus as defined by claim 25, further comprising means in electrical communication with said at least one detector and said grading and sorting means for controlling said grading and sorting means responsive to electrical signals received from said at least one detector.

27. A garment inspecting apparatus as defined in claim 26, further comprising means positioned adjacent at least one detector for directing a gas toward a stitch line of a toe portion of a hosiery garment so as to cause a defect in a stitch line to be more easily recognized by said at least one detector.

28. A method of inspecting a stitch line of a garment comprising:

emitting light closely adjacent a portion of a stitch line of a garment mounted on a mounting member while forming a shadow of the portion of the stitch line; and detecting the presence and absence of defects in the portion of the stitch line responsive to a shadow representative of the presence and absence of defects in the portion of the stitch line of a garment.

29. A method of inspecting a stitch line of a garment as defined by claim 28, further comprising grading a garment into at least one of a plurality of predetermined quality groups responsive to detecting the presence or absence of defects therein.

30. A method of inspecting a stitch line of a garment as defined by claim 28, further comprising directing a gas toward a stitch line of a garment so as to cause a defect in the stitch line to be more easily recognized.

31. A method of inspecting a stitch line of a garment comprising:

emitting light closely adjacent a stitch line of a garment mounted on a mounting member while forming a shadow of the stitch line;

directing a gas toward the stitch line so as to cause a defect in the stitch line to be more easily recognized;

detecting the presence and absence of defects in the stitch line responsive to a shadow representative of the presence and absence of defects in the stitch line of a garment; and grading and sorting a garment into at least one of a plurality of predetermined quality groups responsive to detecting the presence or absence of defects therein.

32. In an apparatus for making garments from blanks including means for receiving and mounting garment blanks in operative association, means for sewing the garment blanks to form seams thereof securing portions of the garment blanks together, and means for conveying the garment blanks to and from said sewing means, the combination of means for optically inspecting and grading the garment blanks based upon the presence and absence of defects in the seams formed, said optical inspecting and grading means comprising a light source operatively associated with said conveying means downstream of said sewing means for directing a beam of light onto the seam after the seam is formed, a detector operatively associated with said conveying means and said light source for detecting any defects in the seam exposed by said light source and for generating a signal indicative of the presence or absence of such defects, and a controller in electrical communication with said detector for grading a garment based upon the presence or absence of defects in the seam.

33. Apparatus according to claim 32 wherein said garment making apparatus is a line closer for receiving respective pairs of hosiery blanks and for forming the blanks into a pair of pantyhose.

34. Apparatus according to claim 32 wherein said garment making apparatus is a toe closer for receiving the leg portions of pantyhose and sewing toe portions thereof to close the same.

* * * * *